US007000186B1

(12) United States Patent
Gropper et al.

(10) Patent No.: US 7,000,186 B1
(45) Date of Patent: Feb. 14, 2006

(54) METHOD AND STRUCTURE FOR ELECTRONICALLY TRANSMITTING A TEXT DOCUMENT AND LINKED INFORMATION

(75) Inventors: Adrian Gropper, Watertown, MA (US); Sean W. Doyle, Somerville, MA (US)

(73) Assignee: Amicas, Inc., Boston, MA (US)

( * ) Notice: Subject to any disclaimer, the term of this patent is extended or adjusted under 35 U.S.C. 154(b) by 0 days.

(21) Appl. No.: 09/304,204

(22) Filed: May 3, 1999

(51) Int. Cl.
*G06F 15/00* (2006.01)
(52) U.S. Cl. ...................................... 715/537; 715/531
(58) Field of Classification Search ................ 707/500, 707/501.1, 530, 531, 512; 715/500, 501.1, 715/530, 531, 537, 512
See application file for complete search history.

(56) References Cited

U.S. PATENT DOCUMENTS

| 4,648,067 A | 3/1987 | Repass et al. |
| 4,648,071 A | 3/1987 | Repass et al. |
| 4,768,099 A | 8/1988 | Mukai ........................ 358/257 |
| 4,817,050 A | 3/1989 | Komatsu et al. ............ 364/900 |
| 4,959,769 A | 9/1990 | Cooper et al. |
| 4,996,662 A * | 2/1991 | Cooper et al. ................. 707/1 |
| 5,001,569 A | 3/1991 | Shigyo ....................... 358/296 |
| 5,029,016 A | 7/1991 | Hiyama et al. ............. 358/403 |
| 5,068,745 A | 11/1991 | Shimura ..................... 358/403 |
| 5,097,418 A * | 3/1992 | Nurse et al. ................. 715/537 |
| 5,146,552 A | 9/1992 | Cassorla et al. |
| 5,276,793 A * | 1/1994 | Borgendale et al. ........ 707/513 |
| 5,319,543 A | 6/1994 | Wilhelm ..................... 364/401 |
| 5,321,520 A | 6/1994 | Inga et al. .................. 358/403 |
| 5,345,551 A | 9/1994 | Shelley et al. |
| 5,384,643 A | 1/1995 | Inga et al. .................. 358/403 |
| 5,416,602 A | 5/1995 | Inga et al. .................. 358/403 |
| 5,432,871 A | 7/1995 | Novik ........................ 382/232 |
| 5,440,678 A * | 8/1995 | Eisen et al. ................. 715/537 |
| 5,493,658 A * | 2/1996 | Chiang et al. .............. 345/709 |
| 5,535,322 A | 7/1996 | Hecht ......................... 395/155 |
| 5,574,573 A | 11/1996 | Ray et al. ................... 358/452 |
| 5,579,519 A * | 11/1996 | Pelletier ..................... 717/139 |
| 5,636,631 A | 6/1997 | Waitz et al. ............. 128/660.1 |
| 5,671,428 A * | 9/1997 | Muranaga et al. .......... 345/751 |
| 5,680,129 A | 10/1997 | Weinberger et al. .......... 341/65 |
| 5,724,582 A | 3/1998 | Pelanek et al. ............. 395/620 |
| 5,734,915 A | 3/1998 | Roewer ...................... 395/773 |
| 5,740,428 A | 4/1998 | Mortimore et al. ......... 395/615 |
| 5,745,392 A | 4/1998 | Ergas et al. ........... 364/715.02 |
| 5,832,476 A | 11/1998 | Tada et al. |
| 5,844,961 A | 12/1998 | McEvoy et al. ........... 378/98.8 |
| 5,845,303 A * | 12/1998 | Templeman ................ 707/514 |

(Continued)

FOREIGN PATENT DOCUMENTS

EP 0 684 565 A1 11/1995

(Continued)

OTHER PUBLICATIONS

Neuwirth et al., The Notes Program : A Hypertext Application for Writing from Source Texts, ACM, Nov. 1987, pp. 121-141.*

(Continued)

*Primary Examiner*—Cong-Lac Huynh
(74) *Attorney, Agent, or Firm*—Jeffrey L. Brandt

(57) ABSTRACT

Method and structure for creating an electronically transmittable document having links therein which does not affect the integrity of the document as provided. The information is formatted to have a text portion, and an endnote portion, the endnote portion being independent of the text portion. The endnote portion includes link information for linking identified portions of the text with other ancillary link information.

20 Claims, 5 Drawing Sheets

U.S. PATENT DOCUMENTS

| | | | |
|---|---|---|---|
| 5,854,888 A * | 12/1998 | Ishikawa et al. | 358/1.17 |
| 5,870,767 A | 2/1999 | Kraft, IV | |
| 5,893,916 A * | 4/1999 | Dooley | 715/523 |
| 5,903,676 A | 5/1999 | Wu et al. | 382/244 |
| 5,905,991 A | 5/1999 | Reynolds | |
| 5,920,877 A * | 7/1999 | Kolster | 715/512 |
| 5,950,207 A | 9/1999 | Mortimore et al. | 707/104 |
| 5,970,499 A | 10/1999 | Smith et al. | 707/104 |
| 5,970,505 A | 10/1999 | Ebrahim | |
| 5,995,976 A * | 11/1999 | Walker et al. | 707/104.1 |
| 6,006,236 A * | 12/1999 | Young | 707/103 R |
| 6,029,167 A * | 2/2000 | Evans | 706/45 |
| 6,064,771 A | 5/2000 | Migdal et al. | 382/232 |
| 6,065,026 A * | 5/2000 | Cornelia et al. | 715/531 |
| 6,067,075 A | 5/2000 | Pelanek | 345/158 |
| 6,067,542 A | 5/2000 | Carino, Jr. | 707/4 |
| 6,073,109 A * | 6/2000 | Flores et al. | 705/8 |
| 6,076,166 A | 6/2000 | Moshfeghi et al. | 713/201 |
| 6,101,407 A | 8/2000 | Groezinger | 600/407 |
| 6,115,640 A * | 9/2000 | Tarumi | 700/100 |
| 6,117,079 A | 9/2000 | Brackett et al. | 600/437 |
| 6,122,403 A | 9/2000 | Rhoads | 382/233 |
| 6,148,304 A * | 11/2000 | de Vries et al. | 707/104.1 |
| 6,154,757 A * | 11/2000 | Krause et al. | 715/530 |
| 6,199,071 B1 * | 3/2001 | Nielsen | 704/3 |
| 6,208,974 B1 * | 3/2001 | Campbell et al. | 705/2 |
| 6,246,404 B1 * | 6/2001 | Feigner et al. | 345/708 |
| 6,253,210 B1 | 6/2001 | Smith et al. | 707/104 |
| 6,260,021 B1 | 7/2001 | Wong et al. | 705/2 |
| 6,269,379 B1 | 7/2001 | Hiyama et al. | 707/104 |
| 6,272,470 B1 | 8/2001 | Teshima | 705/3 |
| 6,286,129 B1 * | 9/2001 | Agarwal et al. | 345/764 |
| 6,287,257 B1 | 9/2001 | Matichuk | 600/437 |
| 6,295,542 B1 | 9/2001 | Corbin | |
| 6,311,192 B1 * | 10/2001 | Rosenthal et al. | 705/38 |
| 6,314,452 B1 | 11/2001 | Dekel et al. | 709/203 |
| 6,351,547 B1 | 2/2002 | Johnson et al. | 382/128 |
| 6,351,761 B1 | 2/2002 | Cantone et al. | 709/202 |
| 6,356,922 B1 * | 3/2002 | Schilit et al. | 715/512 |
| 6,405,226 B1 * | 6/2002 | Alpert et al. | 715/530 |
| 6,411,836 B1 | 6/2002 | Patel et al. | 600/407 |
| 6,430,601 B1 | 8/2002 | Eldridge et al. | 709/206 |
| 6,442,691 B1 * | 8/2002 | Blandford | 340/5.8 |
| 6,449,616 B1 * | 9/2002 | Walker et al. | 707/10 |
| 6,507,410 B1 * | 1/2003 | Robertson et al. | 358/1.18 |
| 6,658,623 B1 * | 12/2003 | Schilit et al. | 715/513 |
| 6,708,311 B1 * | 3/2004 | Berstis | 715/533 |
| 2001/0047517 A1 | 11/2001 | Christopoulos et al. | 725/87 |
| 2001/0051881 A1 | 12/2001 | Filler | 705/3 |
| 2002/0019751 A1 | 2/2002 | Rothschild et al. | 705/3 |
| 2002/0033844 A1 | 3/2002 | Levy et al. | 345/744 |
| 2002/0052551 A1 | 5/2002 | Sinclair et al. | 600/476 |
| 2002/0085026 A1 | 7/2002 | Bocionek et al. | 345/738 |
| 2002/0087359 A1 | 7/2002 | Bocionek | 705/2 |
| 2002/0091765 A1 | 7/2002 | Bocionek | 709/203 |
| 2002/0116227 A1 | 8/2002 | Dick | 705/3 |
| 2002/0122057 A1 | 9/2002 | Maloney | 345/744 |
| 2002/0143862 A1 | 10/2002 | Peterson | 709/203 |

FOREIGN PATENT DOCUMENTS

EP     0 684 566 A1     11/1995

OTHER PUBLICATIONS

Carr et al., Link Servies or Link Agents ?, ACM, 1998, pp. 113-122.*

Tygar, Atomicity in Electronic Commerce, ACM, May 1998, pp. 32-43.*

Quint et al., Combining Hypertext and Structured Documents in Grif, ACM, 1992, pp. 23-32.*

Berrut et al., Indexing Medical Reports in a Multimedia Environment: the RIME experimental approach, ACM 1989, pp. 187-197.*

PR Newswire, EndNote 3.0 : The First Internet Search Client that Creates Bibliographies, Feb. 25, 1998, p. 1.*

Gibson, Create perfect footnote with ease, Inside Corel WordPerfect Suite, Feb. 1999, vol. 4, p. 1, 5 pgs.*

Anonymous, New Add-In Integrates EndNote Plus into Popular Versions of Microsoft Word for Windows, Information Today, Jun. 1996, vol. 13, p. 67, 1 pg.*

Gibson, Create Perfect Footnotes with Ease, Inside Corel WordPerfect Suite, Feb. 1999, vol. 4, iss. 2, p. 1, 5 pgs.*

PCT International Search Report for PCT/US02/13551 dated Nov. 8, 2002.

PCT International Search Report for PCT/US02/37442 dated Aug. 28, 2003.

Anonymous. Desert Radiologists Announces Plans to Launch eMed Wide Access(TM) Technology, DIALOG File 20, *Dialog Global Reporter*, No. 16477601 (May 2, 2001).

* cited by examiner

METHOD AND STRUCTURE FOR ELECTRONICALLY TRANSMITTING A TEXT DOCUMENT AND LINKED INFORMATION

BACKGROUND OF THE INVENTION

This invention is directed to a method for electronically transmitting a text document along with linked information, and in particular, for transmitting a text document with linked information without interfering with or jeopardizing the integrity of the text document.

It is known in the art to transmit text documents such as reports or other types of information as an electronic data stream to a distant terminal by way of Internet, intranet, or the like. It is also known, to provide links within the text which allow the user of the terminal to view one document and retrieve specified associated material that is either associated with or related to the portion of the document text which contains the link.

It is often desirable to combine multiple elements into a single report. For example, written text may be combined with an illustrative image corresponding to that text, or, the text may, in fact, be describing or making comment on what is in the image. By way of example, a medical report describing the symptoms of a patient may include diagnostic images such as MRI, X-ray or the like. More generally, a report that represents interpretation of certain data such as the image or graphs or charts may include illustrative examples from the data. The example data may be included directly within the body of the report or it may be included by reference through a link. Often, these reports are what are known as signature reports, implying that the text of the report has not been tampered with. This is required so that other people making use of the report know that the report can be relied upon.

It is known to combine the illustrative image or data with the text, in effect linking the text through several methods. A first method is to embed the image directly into the text of the reports. However, such an embedding of the image in the report either requires technical know-how by the person creating the report who embeds the image into the report as they are writing it, or requires a second party to embed the image after the report has been completed. However, this brings into question the validity of the report once someone besides the author has manipulated the text to include the images. This is particularly important because any change to the report could result in misdiagnosis or mistreatment. Therefore, embedding pictures into a report after it has been prepared could result in jeopardizing the integrity of the report through inadvertent human error during the embedding process.

Furthermore, it is not always necessary that an image be present to make sense of the medical report. Therefore, embedding the image into the report may be a waste of screen space, text space, and the time of the doctor who is trying to make a quick study of the report.

To overcome these shortcomings, endnotes and web page hyperlinks (HTML) are provided to link the text to a desired address which will retrieve the required illustrative information (link information) as needed and display the link information along with the text. However, conventional endnotes in reports add markers to the body of the report and invalidate the signature. The HTML (hyperlink tags) also modify the body of the report and furthermore require HTML capable terminals in order to process the link.

Therefore, it is desired that a method be provided which allows the linking of text to illustrate data or images as desired which does not modify the text or interfere with the integrity of the text. In other words, it does not invalidate the signature for the report.

SUMMARY OF THE INVENTION

Generally speaking, in accordance with the invention, a structure and method for enabling one or more portions of a text report to be linked to ancillary information without modifying the content of the report is provided. The method includes creating text and counting characters while creating the text. At the desired point where the text is to be linked to other information, a command is given to create a link for the desired characters. The desired characters could be a word, letters or a symbol. The information to be linked is then identified. The character count for the identified portion of the text and the information to be linked, are then combined to form an endnote. When the text has been completed, the endnote is attached to the end of the document.

The endnote includes a marker indicating that an endnote exists, character identifying information which identifies the character in the text which constitutes the linked portion of the text, modification information for modifying the display of the text of those linked characters to signal that a link exists at that position in the text, as well as the address of the information to be linked. The information to be linked (link information) may either be the address of stored images and data at a repository, or maybe another related web site; or any other addressable information.

In a preferred embodiment, the process may be repeated several times to create multiple endnotes within the document. The document may also include an end of document marker such as a doctor's signature or other machine readable marker to facilitate placing of the endnote as well as further maintaining independence between the text and the endnote. Furthermore, the endnote may include a view state of an image stored in a repository, the view state including information such as the address within the repository where the image is stored, the brightness, color, and any annotations or overlays associated with the view state which may have been created in conjunction with the report or image transformation information.

Accordingly, it is an object of the invention to provide an improved method for linking text data with ancillary data without modifying the body of the text data.

Another object of the invention is providing a method for displaying both text reports and associated linked information which maintains the integrity of the report.

Yet another object of the invention is providing a method for displaying a text report and linked information which does not require special hardware or software for interpreting or storing the linkage method.

Still other objects of the invention will, in part, be obvious and will, in part, be apparent from the specification.

The invention accordingly comprises the several steps and the relation of one or more of such steps with respect to each of the others, and the apparatus embodying features of construction, combination of elements, and arrangement of parts which are adapted to affect such steps, all as exemplified in the following detailed disclosure and the scope of the invention will be indicated in the claims.

BRIEF DESCRIPTION OF THE DRAWINGS

For a fuller understanding of the invention, reference is had to the following description in connection with the accompanying drawing, in which.

DETAILED DESCRIPTION OF THE PREFERRED EMBODIMENTS

Figure 1:
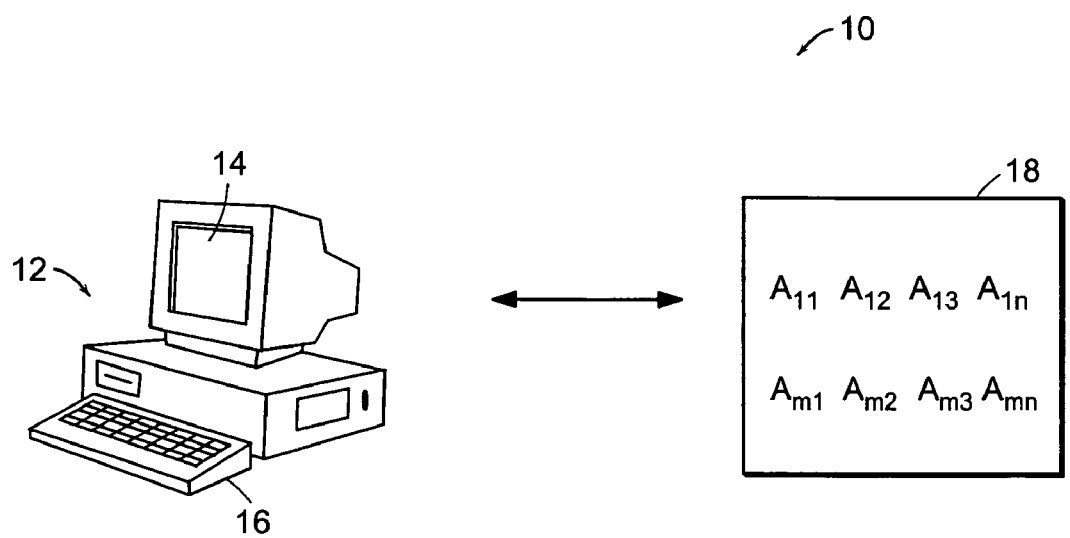
FIG. 1 is a schematic view of a repository system which may be operated in accordance with the invention.
Figure 2:
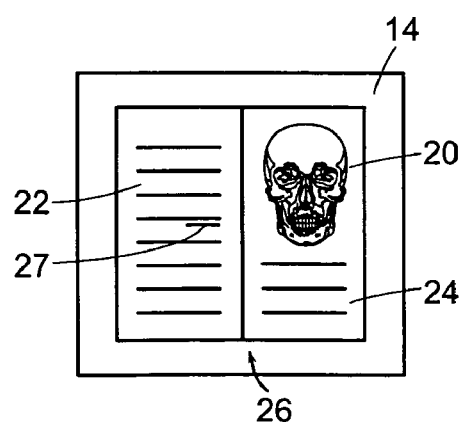
FIG. 2 is a front plan view of a representative image of a display utilizing the method in accordance with the invention.

Reference is now made to FIGS. 1 and 2 which generally depict a system 10 for employing the method for transmitting text and linked information. System 10 includes a terminal 12 including a screen 14, input/output keyboard 16 and a processor and scratch buffer, (not shown) as known in the art for conventional PC terminals. Terminal 12 is linked by either telephone, dedicated wire, radio or the like to a remote (off site) repository 18 of data. By way of example, repository 18 is a repository of X-ray images stored at addresses $a_{11}$ through $a_{mn}$ These images are digitally stored and are transmitted as electronic images to terminal 12 to be displayed. However repository 18 could easily be any addressable local memory.

Generally, when creating a report 26, by way of example, a medical report for a radiologist, the radiologist will retrieve the desired images from repository 18 to be displayed on screen 14 as, for example, image 20 of FIG. 2. At the same time, the radiologist will prepare written text corresponding to the image utilizing keyboard 16 which will be displayed as text 22 on terminal 12. Terminal 12, utilizing the memory and the microprocessor, retains information regarding the stored image such as the address in the repository from which the image was retrieved, the brightness of the image, the color of the image, any annotations to the image which may have been made by the doctor preparing the report and any overlays which may have been added to the report such as written text 22 displayed on terminal screen 14. As the doctor prepares their report 26, they may pull up further images 20 corresponding to that specific portion of the report text 22 currently being created. These images 20 are again retrieved from the repository of images 18. Once the doctor has completed the written text of the report, they place an end mark 28 such as an electronic signature on the report to indicate their approval, and to indicate that the document should not be tampered with.

In order to prevent the document from being tampered with while still maintaining the integrity of the document, the entire report 26 is treated as two separate sections. The written text 22 is treated as one element while the associated pictures 20 are treated as a second separate element; the two being linked.

Figure 3:
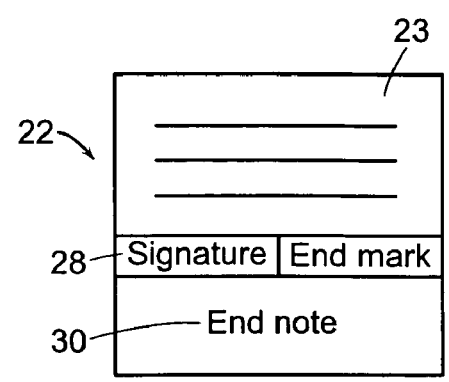
FIG. 3 is a schematic diagram of the format of a document constructed in accordance with the invention.

Reference is now made to FIG. 3 in which the format for the written text portion 22 of report 26 is provided. The written text 22 includes the character string 23 which includes the characters forming the words of the written text 22. A signature 28 including an end of report mark is attached at the end of the characters 23 forming the report 26 and an endnote 30 containing information corresponding to linked portions of the text 22 is attached to the report 26 to the end of the document. When converted into an electronic bit stream, they may be serially transmitted beginning with text 22 and ending with endnote 30. As discussed below, endnote 30 includes the information necessary to link the desired image to the appropriate portion of text 22.

Figure 5:
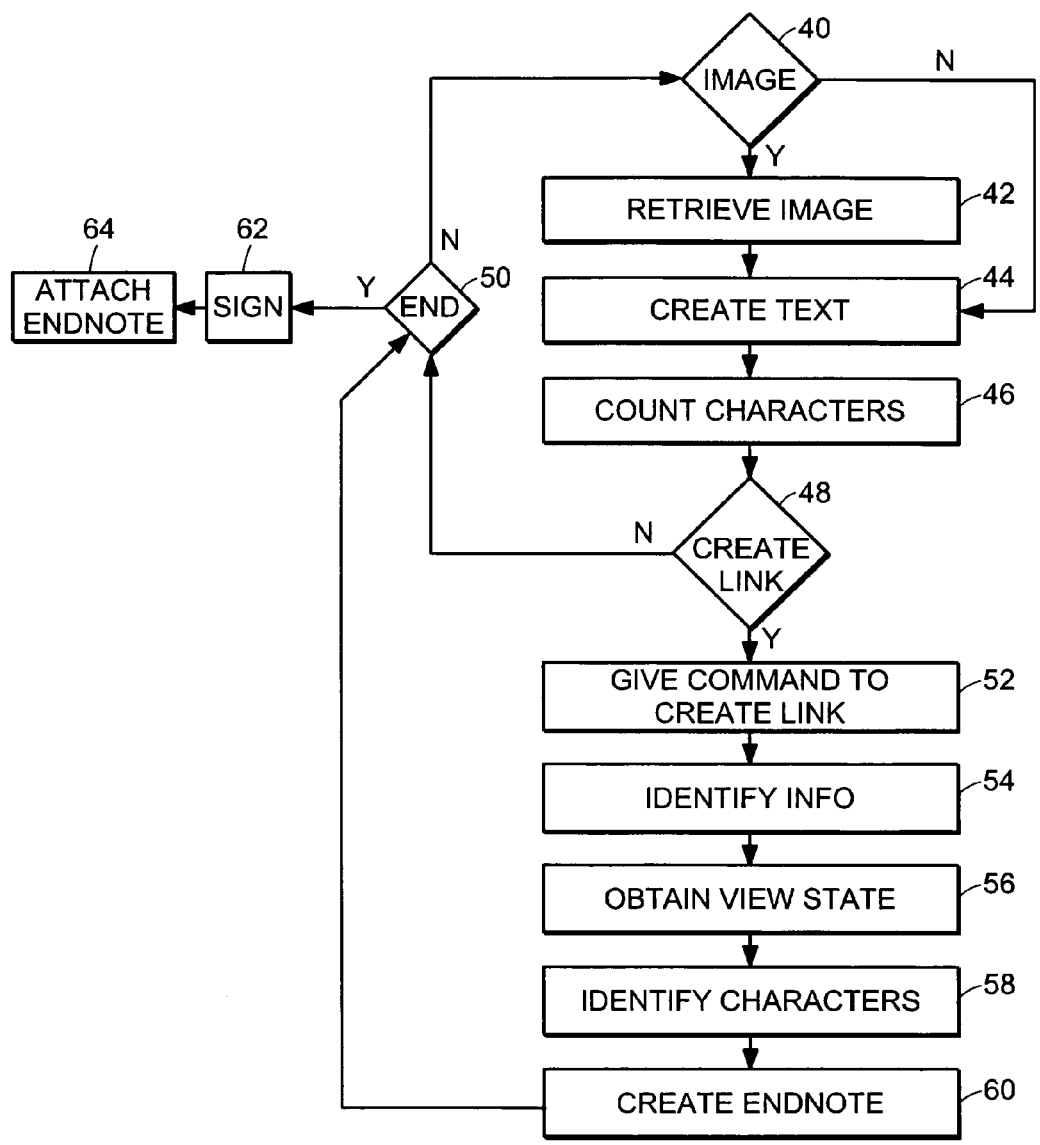
FIG. 5 is a flow chart of a method for creating a document to be transmitted in accordance with the invention.
Figure 6:
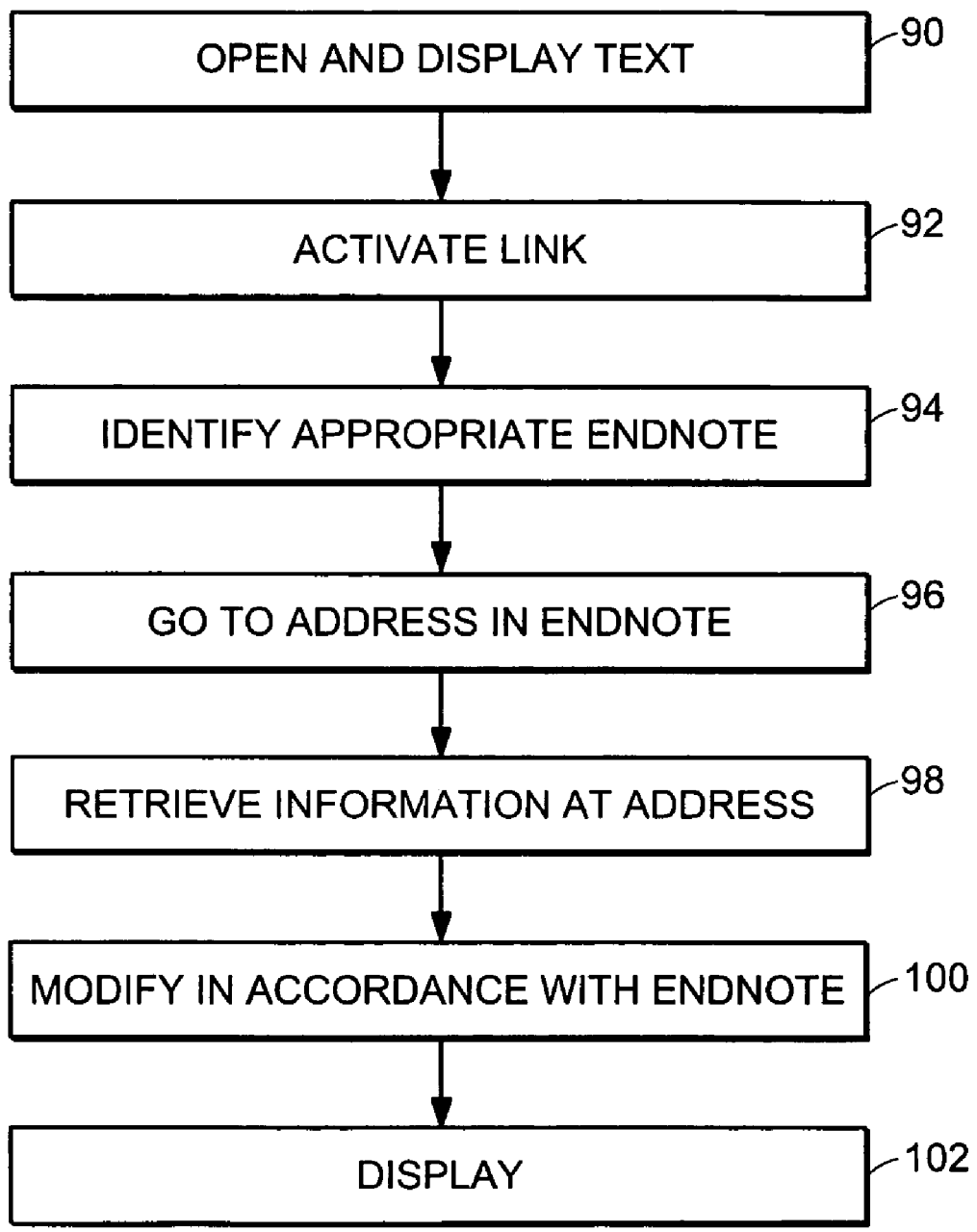
FIG. 6 is a flow chart of the method for processing the document for display in accordance with the invention.

Reference is now made to FIG. 5 in which a flow chart demonstrating the method for creating a report 26 having text 22 linked to images 20 is provided. In a first step 40, it is determined whether or not the doctor wishes to retrieve an image from repository 18. Assuming they are just beginning the report, they may begin by retrieving an image 20 from repository 18 utilizing electronic data retrieval methods in step 42. The doctor would then create text 22 corresponding to that image in a step 44 although, if necessary, the doctor could return to step 42, and retrieve a second or third image 20 prior to creating text 22. As the doctor creates text, terminal 12 counts the characters and/or the lines of the text being typed, in effect, providing an address for each character (letter, number, symbol) within text 22 of the report 26.

If no image is to be retrieved in step 40, then the process moves to step 44 where text 22 is created absent an image. It is then determined whether or not a link should be created between the retrieved image of step 42 and the text of step 44 in a step 48. If no link is to be created either because text 22 does not correspond sufficiently to retrieved image 20, or there is no retrieved image 20, then the process proceeds to a step 50 where it is determined whether the end of text 22 has occurred. If the end of text 22 has not occurred, then the process is returned to step 40 to determine whether or not a first image 20 or following image 20 should be retrieved.

If a link is to be created, a command is given to create a link in step 52. This can be done by identifying the characters which are to be linked by either highlighting utilizing a mouse click technique as is known in the art, indicate the command through keystroke, or orally. The information to be linked to the text is identified in a step 54. This would be the corresponding image 20 in the present example. The system would then obtain the view state information presently being utilized by terminal 12 in accordance with a step 56 to display image 20 with image overlay 24 (if present) in report 26. In a step 58, the system determines which numbered characters, i.e., the address of the characters within text 22 correspond to the link. An endnote 30 is created in step 60 in which the character information is married to the view state information to create the endnote. The process is then returned to step 50 where it is determined whether or not the end of the text has been reached.

Figure 4:
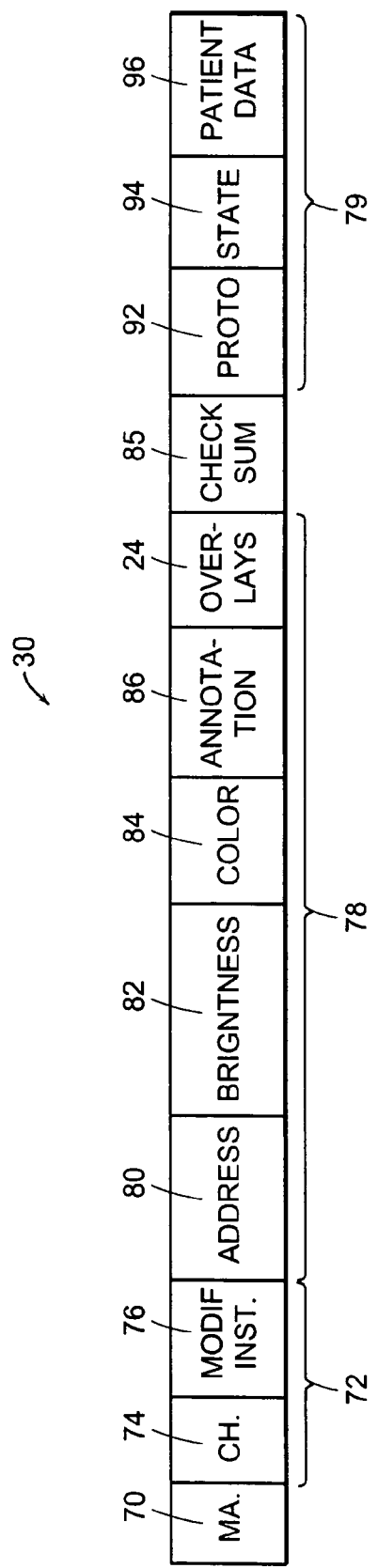
FIG. 4 is a schematic diagram of the format of an endnote constructed in accordance with the invention.

Reference is now made to FIG. 4 in which the format for endnote 30 is provided. The endnote includes two types of information to be used by the system to link the portion of the text 22 with the desired image 20 or other ancillary information; 1) the address of the character within text 22 that corresponds to the linked image 20 as well as 2) view state information pertaining to the linked image 20. Endnote 30 includes an endnote begin marker 70 to indicate to the terminal 12 that an endnote is present. The next characters may be text information 72 including the character address 74 within text 22 such as the line number and/or character number and modification information 76 instructing system 12 how to display text 22 to highlight the character to indicate that the character is a linked portion of text 22; for example, to underline that portion of the text with a link identifier 27 or to change the colors of those characters to indicate to a user at terminal 12 that the text is, in fact, a link.

Endnote 30 includes a view state portion 78 which includes a repository address 80 for the linked information, and may include a brightness control command 82 and color command 84 to instruct terminal 12 how to display image 20. The view state information could also be image transformation information such as magnification, subrectangle or the like. Furthermore, view state 78 may include annotations 86 made during the creation of the report or the overlays 24 to be placed on image 20. With this information, terminal 12 can determine the location of the link within text 22 as well as the information required to pull up the image associated with that link if the link is, in fact, activated. Lastly, endnote 30 includes a check sum 85 to confirm the completeness and accuracy of the endnote as well as to indicate the end of endnote 30.

Once endnote 30 is created in step 60, it is then determined whether or not text 22 is complete in step 50. If text 22 is not complete, it is then determined in step 40 whether an additional image 20 is to be retrieved and, if not, further text 22 created in step 44 and the process is repeated. If it is the end of the written text 22 then an end of document mark 28 such as a signature is applied to indicate the end of the document in a step 62 and the previously created endnotes are attached to the document 26 after the signature in a step 64.

It is preferable that an end mark be provided to separate the endnotes from the text and to indicate to the terminal as well as the user that the text portion has been completely transmitted. However, the same function can be performed by an endnote presence indicator such as endnote begin marker 70, located in each endnote. Because the text is independent of the endnotes, an endnote indicator can also signal to the terminal that text is complete and processing of the endnotes should begin as discussed in detail below.

Once the report has been prepared including the signature and the endnotes, it can also be stored in a repository such as repository 18, a separate report repository (not shown) or in the memory of terminal 12 for later recall and used either by the same doctor or by other persons requiring the information contained in the report in a step 90. To retrieve the report, one would open and display text 22 as retrieved from its storage area. The document is read line by line into a temporary memory at terminal 12 as text until the signature or end of report indicator is read. When this data is encountered, the reading mode is changed from one of downloading text 22 to one of operating on the endnote information. As a result, each line of text is then processed as a separate data structure.

In a preferred embodiment, endnote 30 in its entirety, or merely components thereof, such as view state 78 are in XML language. It is also contemplated that rather than providing view state data 80 through 86, the address 80 of view state 78 could correspond to a web site which is called up in conjunction with the data being read from the report 26. The text 22 in the buffer is then operated upon, for example, by being inserted into a Java Swing document to modify the text in accordance with the instructions 76 stored in endnote 30 to indicate where links exist in the text 22. For example, the text is inserted using standard text attributes and when the text is encountered, it must be displayed as modified. The modifications, such as changing color or underline, are inserted within the text as displayed, not within text 22 itself.

Once text 22 is presented this way, the link is activated through methods known in the art such as a mouse click highlight on screen 14 of terminal 12 or the like in a step 92. The system then identifies the appropriate endnote 30 corresponding to those identified characters by matching the character address data 74 with the position within text 22 that has been activated in step 94. The system then searches for the address 80 contained within the endnote in accordance with a step 96 and retrieves the information stored by way of example in repository 18, at that address in accordance with a step 98. The image is then modified in accordance with the information 82, 84, 86 and 24 in accordance with a step 100 and is displayed as modified in accordance with step 102.

If terminal 12 cannot understand endnote 30 and/or end off text marker 28, then the report will be displayed as shown in FIG. 3 and link identifier 27 will not be shown. However, if terminal 12 does understand endnote 30 and can operate in accordance therewith the report 26 will be displayed as shown in FIG. 2 if a link 27 is selected to be activated by the user. The above explanation was provided in connection with a medical report and associated medical diagnostic images. However, the method works equally well with graphs, or any other associated data which could be linked in the same way images 20 are linked, the main difference being that a view state data would now correspond to manipulation and presentation of other ancillary data. Furthermore, the address link could be to a web site of associated data. Lastly, the example was given by way of a dedicated repository of information linked to a terminal. It should be understood that the repository and terminal can be linked as an Internet link, an intranet link, a dedicated line, or wireless transmission.

By providing the report which is formatted to include an endnote which contains information for linking a portion of the text to other information such as an image, a linked report is provided which is compatible with a legacy transcription system in which hyperlinks can be added to a report after the report is transcribed and signed using existing systems that are not hyperlink aware. Furthermore, it allows the use of preexisting data repositories without the requirement for special equipment. Lastly, even systems that do not interpret the commands of the hyperlink endnote will be able to display text 22 of report 26 without error because the hyperlink information is contained outside of text 22, not within it. The hyperlink endnote may be visible, but it will be visible after the original signature and end of report marks.

As discussed, endnotes formatted as described lend themselves to drafting reports which must be unaltered by their very nature once they have been completed. Such reports form part of a patient's medical records. The medical record is usually the case overview for a patient which includes associated reports, status, and logs describing the procedures, treatments, tests, and doctors' comments for a particular patient.

As medicine is now practiced, the medical report can be thought of as a plurality of protocols and procedures, each protocol and/or procedure having definite steps, or tasks, each task being capable of being performed by different individuals and most likely encouraged to be performed by different individuals. A procedure may have more than one protocol. Any protocol which can be broken up into a plurality of steps can be considered to have a workflow, the workflow being the totality of the steps required to perform a protocol. For example, the steps outlined in connection with FIG. 5 as described above may be considered the definitive steps for the protocol of writing a report containing image data, the workflow being each of the steps from the initial writing of the text or retrieval of data through to the signature and attachment of endnotes. In such a protocol, each of the steps is performed by a single person, that being the commenting doctor. However, the procedures that made the report doable, such as the making of the X-ray images, would be a separate protocol of the overall procedure for diagnosing a patient and could include several steps such as ordering the X-rays to be taken, scheduling the taking of the X-rays, the actual taking of the X-rays, and the development of the X-rays. This protocol includes steps performed by distinct individuals including maybe one doctor and several technicians. Each discrete step is a state within the workflow and can be considered the Workflow State. The endnote described above in creating the report lends itself to tracking the workflow state of a protocol within a procedure.

Figure 7:
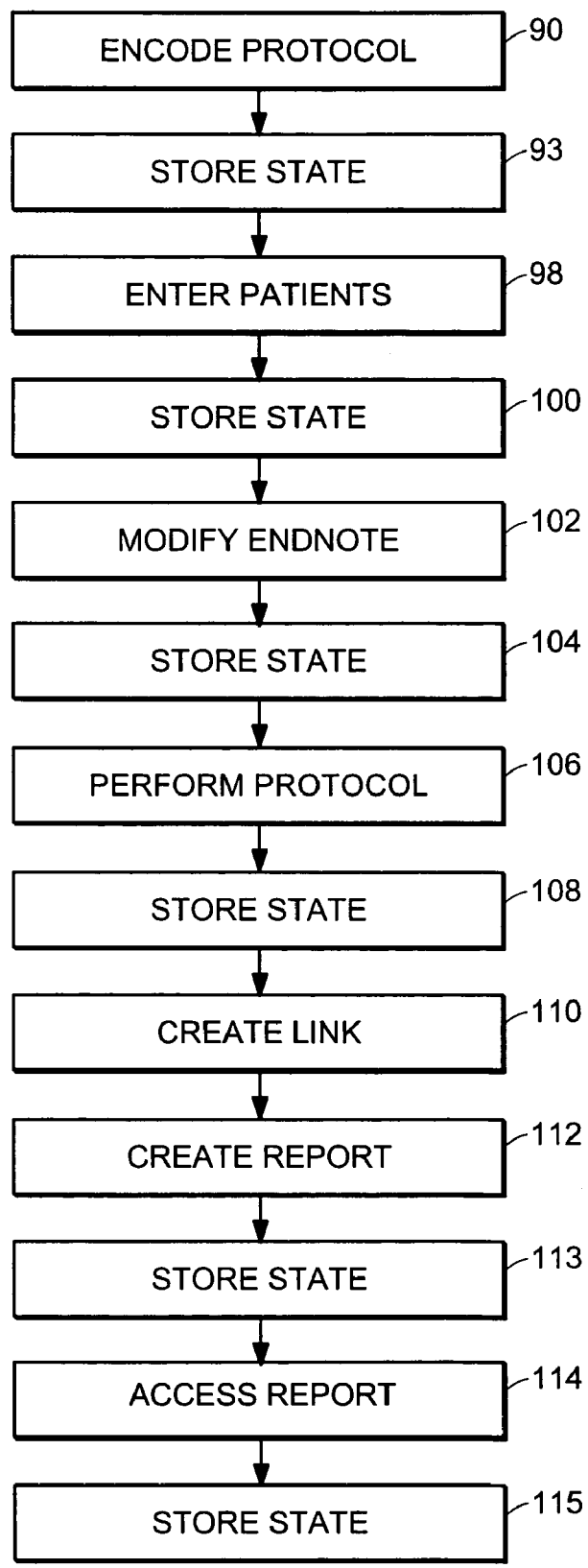
FIG. 7 is a flow chart of the method for creating an endnote in accordance with a second embodiment of the invention.

Reference is now made to FIG. 7 in which a flow chart for utilizing the endnote for tracking the workflow state is provided. An originator of a procedure for treating a patient's condition may publish the procedure as a generic template including several protocols to be performed prior to final treatment. Among each of these protocols may be the preparing of several reports like report 26 described above. The template, published as a web page, may consist of words and images describing the protocols and diagnostic tests associated with the particular treatment. Each of these protocols, for example, will result in a report. The originator of the procedure would also create a generic endnote having a workflow state portion 79 (which may also be in XML language) which will store the protocol and workflow associated with the preparation of the report in generic format to which later patient information can be applied. In a step 90 a protocol for the procedure and the workflow are encoded in the endnote. The inclusion of workflow state portion 79 is only required when tracking work state. The example given with references to FIGS. 1–5 above can obviously be accomplished without a workflow portion 79.

In effect, endnote 30 exists as a shell even though there is no report 26 associated therewith. At this stage, endnote 30 is merely a file on a web site. By way of example, the creating of the template and the creating of the endnote shell may be, in fact, the first two states of the protocol workflow. Therefore, to keep track of the state, the number 2 or the word "endnote" may be stored in a workflow state indicator 94 of endnote 30 in a step 93.

A physician, wishing to make use of the procedure and its protocols may copy the work state for the procedure along with one or more associated templates for creating reports from the web site. The physician would then enter the patient name and other information into the endnote 30 in a patient data portion 96 in a step 98. This is the third step in the protocol and the physician, either manually or automatically, enters either the number 3 in state indicator 94 or the term "patient data" which alerts all users of the endnote of the state of the workflow. This state is stored in a step 100. The physician then may, either manually or automatically, alert the various department that would perform the protocols for a particular procedure.

By way of example, in the next state of the workflow, someone may schedule a diagnostic protocol and modify endnote 30 in a step 102 and changes the state stored in state indicator 94 by either providing the word "schedule" or an incremented number in state indicator 94 in accordance with a step 104. The protocol is then performed, in this case a diagnostic protocol, to obtain the raw data which is stored in repository 18 by way of example in a step 106. Again, the state stored in state indicator 94 is incremented to reflect the completion of this workflow state in a step 108. At this stage, endnote 30 may be modified to contain links to the created data in repository 18 by way of example or a web site as stored in address 80 in a step 110.

In a step 112 a report is created as described above in connection with creating report 26. Generally, a physician opens the report which still contains only an endnote 30 having workflow state information 79. This would correspond to a new state which would be stored in state indicator 94. Then, the doctor would either dictate report 26 or call up the raw data such as the images 20 stored in repository 18 which would correspond to another state along the workflow requiring increment again of the state stored in state indicator 94. The report is then transcribed to form text 23 again incrementing the state stored in indicator 94 and a signature 28 may be added and endnote 30 is modified to add the address information 72 and view state information 78 as described above. Once the report is completed, the workflow state portion is again incremented to reflect the work state in step 113.

Another physician such as the primary care practitioner or another specialist may access the medical record through the endnote which would include the link to report 26 as well as the workflow state stored in indicator 94 as well as the protocols which have been performed in a step 114. Furthermore, the medical record would include a plurality of these reports if necessary. As the physician makes use of the report, this may also be a step within the procedure or protocol and therefore the workflow state indicator 94 is incremented again in a step 115 by changing the number value or storing the term "reviewed".

The report structure allows the addition of information to a report incrementally while remaining compatible with existing report repository and display means. By appending this information (for example, Workflow State, Image Link, Annotation and Digital Signature components) in plain text to the end of the plain text report, compatibility is maintained with the existing report repository, transmission and even display (including paper display). However, when the display is aware of the endnote format, it enables a number of enhancements and manipulations of the information associated with the report. The principal economic value of this invention is that it enables many features and benefits of Internet networks to be added to existing hospital and departmental information systems without the delay and expense of replacing major components of these systems. A further benefit of the invention is that report templates can be developed (by doctors, managed care organizations and pharmaceutical companies) and freely intermixed in the same formal information repositories. The different reports can carry vastly different protocols and might, in a preferred embodiment put this information in XML format.

By providing an endnote which can be used in connection with the report which forms part of a medical record, it is possible to create an electronic medical record including records of past procedures, protocols and logs. As a result, medical records linking a plurality of reports, protocols and procedures can be electronically stored, linked and accessed.

It will thus be seen that the objects set forth above, among those made apparent from the preceding description are efficiently attained and, since certain changes may be made in carrying out the above method and the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific structures of the invention herein described and all statements of the scope of the invention which, as a matter of language, might be said to fall there between.

What is claimed is:

1. A computer program product embodied in a computer readable medium storing instructions to control the operation of a computer to generate an electronically transmittable linked report, the computer program product operable with a computer to perform the steps comprising:
   generating a text section; and
   generating an endnote section, the endnote section a) being independent of the text section, b) including information for linking portions of text contained in the text section to predetermined link information, and c) comprising at least one endnote, said endnote including character information for identifying the address within the text which is to be linked and view state information, the view state information further including at least a link information address corresponding to the address from which the link information can be retrieved.

2. The computer program product of claim 1, wherein said view information also includes image brightness information, image color information, annotations to an image, image overlay and transformations.

3. The computer program product of claim 1, wherein said view state information includes an external web site address.

4. The computer program product of claim 1, wherein said link information address includes the address within a repository of stored images for a predetermined image.

5. The computer program product of claim 1, wherein said view state information in is extensible mark up language.

6. The computer program product of claim 1, wherein said endnote includes a check sum.

7. The computer program product of claim 1, wherein said endnote includes a workflow state information portion.

8. A method for creating a linked report which is electronically transmittable through a terminal comprising the steps of:
   creating a text for a report;
   counting at least the characters within the text to obtain a character address for each character with in the text;
   retrieving link information to be displayed along with the text in association with a predetermined portion of the text, the link information including an image;
   obtaining view state information for the image, the view state information including at least a link information address corresponding to the address from which the link information can be retrieved;
   creating an independent endnote including the character address of the predetermined portion and the link information address; and
   attaching the endnote to the report after the text, without adding or deleting characters from the text.

9. The method of claim 8, wherein said endnote further includes image brightness information, image color information, image annotations, and image overlay.

10. The method of claim 8, wherein said endnote includes text display modification instructions for modifying the display of the predetermined portion of the text to indicate that characters contained in the predetermined portions are linked.

11. The method of claim 8, further comprising the step of providing an end of text marker after the text and attaching the endnote to the report after the end of text marker.

12. The method of claim 11, wherein the end of text marker is a signature.

13. A method for creating a report based upon a protocol including the steps of:
   creating an endnote having a workflow state portion and encoding the protocol in said workflow state portion;
   the endnote including a workflow state indicator, and storing a workflow state in the workflow state indicator;
   performing a step in the protocol and changing the workflow state value stored in said workflow state indicator to indicate the performed step has been completed;
   modifying the endnote to contain data for identifying a patient to which the protocol is to be performed;
   increasing the workflow state value stored in the workflow state indicator;
   modify the endnote to include specific protocol steps;
   incrementing the workflow state value stored in the workflow state portion to indicate modification of the endnote;
   performing the protocol; and
   incrementing the workflow state value stored in the workflow state indicator to indicate performance of the protocol.

14. The method of claim 13, further comprising the steps of:
   creating a link to results of the performed protocol;
   incrementing the workflow state value in the workflow state indicator to indicate the creation of the link;
   creating a report by modifying the endnote to include link and report address information; and
   incrementing the workflow state value in the workflow state indicator.

15. The method of claim 14, wherein the report includes text and further comprising the steps of:
   creating the text;
   counting at least the characters within the text to obtain a character address for each character within the text;
   obtaining view state information for said image, the view state information including at least a link information address corresponding to the address from which the results of the performed protocol can be retrieved; and
   said endnote including the character address of a predetermined portion of the text and the link information address.

16. The method of claim 15, wherein said endnote further includes image brightness information, image color information, image annotations, and image overlay.

17. The method of claim 15, wherein said endnote includes text modification instructions for modifying the display of the predetermined portion of the text to indicate that characters contained in the predetermined portions are linked.

18. The method of claim 15, wherein the results of the performed protocol include an image.

19. The method of claim 15, further comprising the step of providing an end of text marker after the text and attaching the endnote to the report after the end of the text marker.

20. The method of claim 19, wherein the end of text marker is a signature.

* * * * *

UNITED STATES PATENT AND TRADEMARK OFFICE
CERTIFICATE OF CORRECTION

PATENT NO. : 7,000,186 B1 Page 1 of 1
APPLICATION NO. : 09/304204
DATED : February 14, 2006
INVENTOR(S) : Adrian Gropper and Sean W. Doyle It is certified that error appears in the above-identified patent and that said Letters Patent is hereby corrected as shown below:

On Title Page in Column 2 (Foreign Patent Documents), Line 1, after "11/1995" insert - - G06F/17/30 - -.

On Title Page, Page 2, in Column 2 (Foreign Patent Documents), Line 1, after "11/1995" insert - - G06F/17/30 - -.

Title Page, Page 2, Col. 2, in Column 2 (Other Publications), Line 13, delete "vol." and insert - - Vol. - -, therefor.

Title Page, Page 2, Col. 2, in Column 2 (Other Publications), Line 23, delete "Anonymous." and insert - - Anonymous, - -, therefor.

On Title Page, Page 2, Col. 2, in Column 2 (Other Publications), Line 23, insert - - " - - before "Desert".

Title Page, Page 2, Col. 2, in Column 2 (Other Publications), Line 24, after "Technology," insert - - " - -.

In Column 1, Line 66, delete "require" and insert - - requires - -, therefor.

In Column 3, Line 36, after "$a_{mn}$" insert - - . - -.

In Column 9, Line 37, in Claim 5, delete "in is" and insert - - is - -, therefor.

Signed and Sealed this

First Day of August, 2006

JON W. DUDAS
*Director of the United States Patent and Trademark Office*